United States Patent [19]

Son

[11] 4,326,063

[45] Apr. 20, 1982

[54] HIGH MOLECULAR WEIGHT PIPERIDINE DERIVATIVES AS UV STABILIZERS

[75] Inventor: Pyong-Nae Son, Akron, Ohio

[73] Assignee: The B. F. Goodrich Company, Akron, Ohio

[21] Appl. No.: 171,775

[22] Filed: Jul. 24, 1980

[51] Int. Cl.³ ............................................ C07D 401/08
[52] U.S. Cl. .................... 546/191; 546/223; 524/103
[58] Field of Search ................................ 546/191, 223

[56] References Cited

U.S. PATENT DOCUMENTS

| | | | |
|---|---|---|---|
| 3,480,635 | 11/1969 | Altwicker | 546/223 |
| 4,021,432 | 5/1977 | Holt et al. | |
| 4,031,095 | 6/1977 | Ramey et al. | |
| 4,075,165 | 2/1978 | Soma et al. | |
| 4,190,571 | 2/1980 | Lai et al. | 546/223 |
| 4,207,228 | 6/1980 | Lai et al. | 546/223 |

OTHER PUBLICATIONS

March "Advanced Organic Chemistry" (McGraw-Hill) (1968) pp. 668-670.
Pauling "General Chemistry" (Third Edition) (1970) (Freeman) pp. 408-409.

*Primary Examiner*—Robert T. Bond
*Attorney, Agent, or Firm*—John H. Faro

[57] ABSTRACT

Process for the selective reductive alkylation of a cyclic diamine by catalytic condensation of the cyclic diamine with a hetercyclic ketone. In the process described herein, the reaction conditions and catalyst which are selected are directive for the synthesis of the N,N' substituted cyclic diamine. The compounds produced according to this procedure are readily isolated and are effective as UV stabilizers.

5 Claims, No Drawings

HIGH MOLECULAR WEIGHT PIPERIDINE DERIVATIVES AS UV STABILIZERS

BACKGROUND OF THE INVENTION

1. Field of the Invention

This invention relates to a method of preparation and compositions prepared thereby. More specifically, this invention is directed to a process which is directive for the synthesis of highly effective UV stabilizer compounds and the products of such process.

2. Description of the Prior Art

The reductive alkylation of amines is well known and can be readily achieved by reaction of an amine and an aliphatic aldehyde, or an aliphatic ketone, in the presence of hydrogen and an appropriate catalyst. Ordinarily, the pressure and temperature conditions prevailing during such reaction must also be carefully selected in order to drive the reaction in the direction of the desired product. Where a diamine is subjected to reductive alkylation under normal conditions, a mixture of products is usually obtained. This mixture will contain compounds having varying degrees of alkylation, (i.e. diamines in which the degrees of alkylation is incomplete and reaction by-products comprising hydroxyl functional compounds corresponding to the carbonyl functional reactant).

The products of the reductive alkylation of diamines are difficult to separate from one another and, therefore, this procedure generally is regarded as inefficient for the preparation of the N,N' alkylated compound. The alkylation of amine functional compounds with a cyclic ketone, when attempted under ordinary processing conditions, also yields similar product mixtures.

But for the difficulty in obtaining acceptable yields and separation of the products obtained by such synthesis, the reductive alkylation of diamine would provide a convenient method for the synthesis of multifunctional stabilizer compounds. For example, it is known that certain keto-functional hindered amines are highly effective UV stabilizers (see U.S. Pat. Nos. 4,190,571 and 4,207,228). These compounds can also reportedly be appended from a polymer backbone and the resultant polymer also be suitable as UV stabilizer.

In comparing the relative advantages of nonpolymeric versus the polymeric stabilizers, it would appear, from the technical literature, that the polymeric stabilizers are more resistant to extraction and diffusion within the polymeric materials, whereas, the non-polymeric systems provide a greater degree of uniformity protection, at comparable concentrations, than the corresponding polymeric system. It would thus appear that each of the foregoing types of stabilizers do suffer from some inherent disadvantage and that an intermediate species of compound would be preferable; namely, one having the resistance to extraction of a polymeric stabilizer and yet the ease of uniformity of distribution within the polymer of a non-polymeric stabilizer.

But for the problems inherent in the reductive alkylation from diamines, the aforementioned keto-functional hindered amines would serve as an attractive alkylating agent and the resultant product could fill this intermediate role. Thus, there is a continuing need for an effective method to synthesize stabilizer compounds so as to render them immobile within a plastic film or fiber and yet provide acceptable protection at low stabilizer concentrations in order to minimize the effect of such stabilizers on the physical properties and processing characteristics of the stabilized plastic.

SUMMARY OF THE INVENTION

Accordingly, it is the object of this invention to remedy the above as well as related deficiencies in the prior art.

More specifically, it is the principal object of this invention to provide an improved process for the reductive alkylation of diamines.

It is yet another object of this invention to provide an improved process which is directive for the synthesis for N,N' alkylated diamines at high yields.

It is still yet another object of this invention to provide an improved process which is adaptive for the synthesis of multi-functional UV stabilizers from diazacyclo alkanones.

Additional objects of this invention include the provision of novel products prepared by the improved synthesis and the stabilization of UV sensitive plastics with such novel products.

The above and related objects are achieved by providing an improved process for the reductive alkylation of diamines, especially cyclic diamines, at high yields. According to this process, a cyclic diamine is contacted in a reducing atmosphere, and under a pressure of at least 1500 psi, with a carbonyl functional hindered amine and a catalytic effective amount of platinum; and preferably platinum on a carbon support. Good results are obtained when the temperature of the reactants is maintained at at least about 60° C. and preferably at the refluxing temperature of the reaction medium.

The cyclic diamine suitable for use in this process is preferably selected from among the compounds of the following formula:

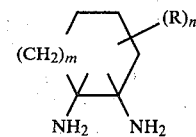

wherein
R is alkyl of 1 to 6 carbon atoms
m is 1 to 4
n is 0 to 3

In one of the preferred embodiments of this invention, the cyclic diamine is a cyclo aliphatic compound of 6 to 10 carbon atoms.

The carbonyl functional hindered amine which is suitable for use in this process is selected from among the compounds of the formula:

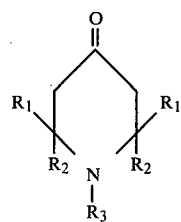

wherein $R_1$ and $R_2$ are independently selected from alkyl of 1 to 6 carbon atoms; and $R_3$ is selected from among hydrogen, hydroxyl, alkyl of 1 to 6 carbon atoms, aryl, aralkyl or alphyl.

The mole ratio of carbonyl functional hindered amine to cyclic diamine in the reaction medium is preferably 1:2, and most preferably a stoichiometric excess of alkylating agent (carbonyl functional hindered amine) should be present relative to the cyclic diamine. Good results are consistently obtained when the catalyst concentration in the charge is about 0.4 gram of 10 weight percent platinum on carbon per 0.1 mole of alkylating agent.

DESCRIPTION OF THE INVENTION INCLUDING PREFERRED EMBODIMENTS

This invention provides an efficient, high yield process for the reductive alkylation of diamines. Through the proper selection of process conditions and catalyst concentration it is possible to obtain the N,N' alkylated diamine to the almost total exclusion of other products in the charge.

Reactants suitable for use in this process include (a) a cyclic diamine, (b) a carbonyl functional cyclic compound, and (c) a platinum catalyst. The reaction medium in which the above ingredients are combined in accordance with the process of this invention, is preferably a polar organic solvent, such as an aliphatic (lower alkyl) alcohol; including methanol, propanol and butanol. The order of addition of the ingredients to the reaction medium is not critical, however, the reactants are generally charged first, the reactor purged of air with hydrogen at the same time the vessel is pressurized and the catalyst thereafter introduced. The reactants are then brought to the desired temperature and maintained under mild agitation for a period of time sufficient to achieve essentially complete alkylation of the amine. This reaction interval is ordinarily from about 120 to 300 minutes, depending upon the reaction temperature selected.

The cyclic diamines suitable for use in this process can have a structural formula as set forth hereinabove and are preferably selected from 1,2-diamino-cyclohexane, 1,2-diaminocycloheptane and 1,2-diamino-cyclooctane. The foregoing cyclic diamines are generally readily available commercially or can be prepared by techniques and with equipment described in the open literature. For example, 1,2-diamino cyclohexane is available from E. I. duPont de Nemours of Wilmington, Delaware; or, can be prepared according to the procedures described in the open literature.

The catalyst employed in this process is metallic platinum, preferably on a carbon support. The amount of catalyst relative to the reactants is of critical importance to the directivity of such synthesis and should be present at a concentration from 4-10 grams of 10 weight percent platinum on carbon for each mole of alkylating agent.

The reaction medium suitable for use in this process can be virtually any anhydrous, olar solvent such as the lower alkyl alcohols, (i.e. methanol, propanol, and butanol).

EXAMPLES

The Examples which follow have been provided to further define, describe and illustrate the parameters of the improved process of this invention. The apparatus and techniques used in the implementation of this improved process are standard or as hereinbefore described. Parts and percentages appearing in such Examples are by weight unless otherwise indicated.

EXAMPLE I

Preparation of N-(2,2,6,6-tetramethylpiperidine-4-yl)-1,2-diaminocyclohexane

In a 110 ml autoclave are charged 17.3 g (0.1 mole) of 2,2,6,6-tetramethyl-4-piperidone, 30 ml methanol, 11.4 g (0.1 mole) of 1,2-diaminocyclohexane, and 0.10 g of 10% platinum on carbon. After reacting under 800 psi hydrogen gas at 80° C., the reaction mixture is cooled, filtered, and concentrated. Desired products are isolated by a fractional distillation. The fraction with a bp 124°-5° C./0.80 mm Hg is N-(2,2,6,6-tetramethylpiperidin-4-yl)-1,2-diamino-cyclohexane, while the one with bp 179°-180° C./0.70 mm Hg is N,N'-bis(2,2,6,6-tetramethylpiperidin-4-yl)-1,2-diamino-cyclohexane. The yield was 47.6 and 12.6%, respectively.

Called for $C_{15}H_{31}N_3$:C, 71.09; H, 12.33; N, 16.58. Found: C, 71.17; H, 12.09; N, 16.59.

Called for $C_{24}H_{48}N_4$: C, 73.41; H, 12.32; N, 14.27. Found: C, 73.33; H, 12.11; N, 14.19.

EXAMPLE II

Preparation of N,N'-bis(2,2,6,6-tetramethylpiperidin-4-yl)-1,2-diaminocyclohexane—The title compound is prepared according to the procedures described in Example I. 31.05 g (0.2 mole) of 2,2,6,6-tetramethyl-4-piperidone and 22.84 g (0.2 mole) of 1,2-diaminocyclohexane is reacted in the presence of 50 ml of methanol and 0.30 g of 10% platinum on carbon under 1000 psi $H_2$ pressure at 80° C. About 83% (by GC) of N-(2,2,6,6-tetramethylpiperidin-4-yl)-1,2-diaminocyclohexane is formed.

The table which follows clearly illustrates the effect of varying the process conditions and catalyst concentration on the yield of the N,N' alkylated diamine.

TABLE I

| Experiment No | **Mole (A) | **Mole (B) | ml of MeOH | g of Catalyst | CG of Crude Product (%) | | | Reaction Temp & Press |
|---|---|---|---|---|---|---|---|---|
| | | | | | **(C) | **(D) | **(E) | |
| 1. | 634 | 0.10 | 0.1 | 30ml | 0.10 g 10% Pt on C | 15.8 | 70.7 | 13.8 | 80° C./ 800 psi |
| 2. | 788 | 0.10 | 0.1 | 25ml | 0.20 g 10% Pt on C | 1.4 | 97.9 | 4.0 | 60° C./ 1500 psi |
| 3. | 828 | 0.10 | 0.05 | 25ml | 0.20 g 10% Pt on C | 74.8 | 14.9 | 6.9 | 60° C./ 1500 psi |
| 4. | 836 | 0.106 | 0.05 | 25ml | 0.40 g 10% Pt on C | 81.4 | 8.7 | 8.9 | 60° C./ 1500 psi |
| 5. | 848 | 0.10 | 0.05 | 25ml | 0.80 g 10% Pt on C | 84.1 | 9.8 | 5.5 | 60° C./ 1500 psi |
| 6. | 858 | 0.10 | 0.05 | 25ml | 1.55 g 10% Pt on C | 71.9 | 14.2 | 8.8 | 60° C./ 1500 psi |
| 7. | 860 | 0.10 | 0.05 | 20ml | 0.8 g | 71.1 | 16.4 | 11.4 | 60° C./ |

TABLE I-continued

| Experiment | | **Mole (A) | **Mole (B) | ml of MeOH | g of Catalyst | CG of Crude Product (%) | | | Reaction Temp & Press |
|---|---|---|---|---|---|---|---|---|---|
| No | | | | | | **(C) | **(D) | **(E) | |
| 8. | 878 | 0.108 | 0.05 | 25ml | 0.6 g 10% Pt on C | 92.4 | — | 0.5 | 2000 psi 60° C./ |
| 9. | 888 | 0.108 | 0.05 | 25ml | 0.6 g 10% Pt on C | 92.0 | — | 2.1 | 1500 psi 60° C./ 1400 psi |
| 10. | 1202A* | 0.108 | 0.05 | 25ml | 0.6 g 10% Pt on C | 97.6 | 2.4 | — | 70° C./ 1500 psi |
| 11. | 1208A* | 0.108 | 0.05 | 25ml | 0.6 g 10% Pt on C | 94.0 | 5.1 | — | 60° C./ 1500 psi |
| 12. | 1214A* | 0.162 | 0.075 | 37ml | 0.9 g 10% Pt on C | 95.0 | 3.7 | 0.5 | 60° C./ 1500 psi |
| 13. | 1214 | 0.162 | 0.075 | 37ml | 0.9 g 10% Pt on C | 86.1 | 3.0 | 9.7 | 60° C./ 1500 psi |
| 14. | 1234A* | 0.143 | 0.05 | 25ml | 0.6 g 10% Pt on C | 85.5 | 11.0 | 1.3 | 60° C./ 1500 psi |
| 15. | 1234 | 0.1043 | 0.05 | 25ml | 0.6 g 10% Pt on C | 78.9 | 9.5 | 9.5 | 60° C./ 1500 psi |
| 16. | 1280 | 0.162 | 0.075 | 37ml | 1.0 g 10% Pt on C | 81.7 | 6.6 | 10.9 | 60° C./ 1500 psi |

*A stands for the sample after removal of compound (E)
C = Carbon
**A is 2,2,6,6-tetramethyl-4-piperidone
**B is 1,2-diaminocyclohexane
**C is N,N'-bis(2,2,6,6-tetramethylpiperdine-4-yl)1,2-diamonocyclohexane
**D is N-(2,2,6,6-tetramethylpiperdine-4-yl)-1,2-diaminocyclohexane
**E is 4-hydroxy-2,2,6,6-tetramethylpiperdine

TABLE II

XENON WEATHERMETER DATA OF 20 MIL (PLAQUES) POLYPROPYLENE SAMPLES*

| | | Failure** time (hrs) |
|---|---|---|
| 1. | No UV stabilizer | 230 |
| 2. | Cyasorb 531 (0.25 part) | 1040 |
| 3. | N,N'-bis(2,2,6,6-tetramethyl-piperdine-4-yl)1,2-diamono-cyclohexane (0.25 part) | 3020 |
| 4. | N-2(2,2,6,6-tetramethyl-piperdine-4-yl)-1,2-diamino-cyclohexane (0.25 part) | |

*All samples contain Goodrite 3125 as and antioxidant.
**Time to reach 50% of the original tensile.

I claim:

1. A compound of the formula wherein X is

R being selected from alkyl of 1–6 carbon atoms; with $R_1$ and $R_2$ being independently selected from the group consisting of alkyl of 1–6 carbon atoms; $R_3$ being selected from the the group consisting of hydrogen, hydroxyl, alkyl of 1–6 carbon atoms, benzyl;

m is 1 to 4; and n is 0–3.

2. A compound of claim 1 wherein the cyclic diamine portion of said compounds is derived from the group consisting of 1,2-diamino-cyclohexane, 1,2-diaminocycloheptane, and 1,2-diamino-cyclooctane.

3. A compound of claim 2 wherein $R_1$ and $R_2$ are methyl groups.

4. A compound of claim 1, N-(2,2,6,6-tetramethyl-piperidine-4-yl)-1,2-diaminocyclohexane.

5. A compound of claim 1, N,N'-bis(2,2,6,6-tetramethylpiperidine-4-yl)-1,2-diaminocyclohexane.

* * * * *